(12) United States Patent
Hartley et al.

(10) Patent No.: US 8,858,584 B2
(45) Date of Patent: Oct. 14, 2014

(54) EMERGENCY TRANSECTION DEVICE

(75) Inventors: David E. Hartley, Subiaco (AU); John Alvarez, Claremont (AU)

(73) Assignee: Cook Medical Technologies LLC, Bloomington, IN (US)

( * ) Notice: Subject to any disclaimer, the term of this patent is extended or adjusted under 35 U.S.C. 154(b) by 1487 days.

(21) Appl. No.: 11/983,151

(22) Filed: Nov. 7, 2007

(65) Prior Publication Data

US 2008/0132937 A1  Jun. 5, 2008

Related U.S. Application Data

(60) Provisional application No. 60/857,230, filed on Nov. 7, 2006.

(51) Int. Cl.
*A61M 29/00* (2006.01)
*A61B 17/12* (2006.01)
*A61M 29/02* (2006.01)
*A61M 25/10* (2013.01)

(52) U.S. Cl.
CPC ...... *A61M 25/1011* (2013.01); *A61B 17/12136* (2013.01); *A61M 29/02* (2013.01); *A61M 2025/1095* (2013.01); *A61B 17/12045* (2013.01); *A61B 17/12109* (2013.01)
USPC .................. 606/194; 604/101.05; 604/102.02

(58) Field of Classification Search
CPC . A61M 25/1011; A61M 25/10; A61M 25/04; A61M 1/36; A61M 25/00
USPC .......... 606/194; 604/101.01, 101.03, 101.05, 604/102.01, 102.02, 102.03, 103.03, 164.1, 604/167.01, 236, 167.06
See application file for complete search history.

(56) References Cited

U.S. PATENT DOCUMENTS

| | | | | |
|---|---|---|---|---|
| 4,180,076 A | * | 12/1979 | Betancourt | 604/101.03 |
| 4,636,195 A | * | 1/1987 | Wolinsky | 604/509 |
| 4,696,668 A | * | 9/1987 | Wilcox | 604/28 |
| 4,813,935 A | * | 3/1989 | Haber et al. | 604/99.02 |
| 4,832,688 A | * | 5/1989 | Sagae et al. | 604/509 |
| 4,946,449 A | * | 8/1990 | Davis, Jr. | 604/256 |
| 4,950,226 A | * | 8/1990 | Barron | 604/8 |
| 5,135,474 A | * | 8/1992 | Swan et al. | 604/8 |
| 5,250,060 A | * | 10/1993 | Carbo et al. | 606/159 |
| 5,312,344 A | * | 5/1994 | Grinfeld et al. | 604/101.05 |
| 5,380,284 A | * | 1/1995 | Don Michael | 604/101.03 |
| 5,405,322 A | * | 4/1995 | Lennox et al. | 606/28 |
| 5,411,479 A | * | 5/1995 | Bodden | 604/101.03 |
| 5,478,309 A | * | 12/1995 | Sweezer et al. | 604/6.14 |

(Continued)

*Primary Examiner* — Darwin Erezo
*Assistant Examiner* — Erin Colello
(74) *Attorney, Agent, or Firm* — Richard J. Godlewski

(57) ABSTRACT

An emergency transection intervention device has an elongated catheter (4) with a movable nose cone dilator (8) temporarily closing off the first end of the elongate catheter, a haemostatic seal (6) on a second end of the catheter and closing off the second end of the elongate catheter. First and second inflatable balloons (12, 14) are spaced apart on the elongate catheter, and there is an aperture (16) in the elongate catheter between the balloons and the haemostatic seal. The emergency transection intervention device can be deployed into a blood vessel of the human or animal body, during an emergency procedure for instance, with the balloons positioned either side of a damaged portion of the vessel and the balloons inflated such that a region of the vessel between the balloons is isolated. The nose cone dilator can then be advanced to allow blood flow through the elongate catheter and exit through the aperture in the elongate catheter to bypass the damaged portion of the vessel during repair.

8 Claims, 4 Drawing Sheets

(56) References Cited

U.S. PATENT DOCUMENTS

| | | | |
|---|---|---|---|
| 5,484,412 A * | 1/1996 | Pierpont | 604/101.03 |
| 5,599,307 A * | 2/1997 | Bacher et al. | 604/101.05 |
| 5,695,499 A * | 12/1997 | Helgerson et al. | 606/108 |
| 5,810,757 A * | 9/1998 | Sweezer et al. | 604/6.06 |
| 5,868,702 A * | 2/1999 | Stevens et al. | 604/96.01 |
| 5,947,977 A * | 9/1999 | Slepian et al. | 606/108 |
| 6,017,352 A * | 1/2000 | Nash et al. | 606/153 |
| 6,083,198 A * | 7/2000 | Afzal | 604/101.01 |
| 6,165,196 A * | 12/2000 | Stack et al. | 606/194 |
| 6,167,886 B1 * | 1/2001 | Engel et al. | 128/885 |
| 6,234,995 B1 * | 5/2001 | Peacock, III | 604/96.01 |
| 6,241,699 B1 * | 6/2001 | Suresh et al. | 604/7 |
| 6,253,770 B1 * | 7/2001 | Acker et al. | 128/899 |
| 6,293,920 B1 * | 9/2001 | Sweezer et al. | 604/6.14 |
| 6,322,586 B1 * | 11/2001 | Monroe et al. | 623/1.11 |
| 6,325,776 B1 * | 12/2001 | Anderson et al. | 604/8 |
| 6,330,884 B1 * | 12/2001 | Kim | 128/898 |
| 6,398,752 B1 * | 6/2002 | Sweezer et al. | 604/6.14 |
| 6,443,965 B1 * | 9/2002 | Gifford et al. | 606/153 |
| 6,485,500 B1 * | 11/2002 | Kokish et al. | 606/194 |
| 6,569,146 B1 * | 5/2003 | Werner et al. | 604/509 |
| 6,613,081 B2 * | 9/2003 | Kim et al. | 623/1.15 |
| 6,726,651 B1 * | 4/2004 | Robinson et al. | 604/101.01 |
| 7,402,168 B2 * | 7/2008 | Sanderson et al. | 623/1.11 |
| 7,862,541 B2 * | 1/2011 | Jeffrey et al. | 604/96.01 |
| 2001/0012946 A1 * | 8/2001 | MacKenzie et al. | 606/185 |
| 2002/0198492 A1 * | 12/2002 | Miller et al. | 604/96.01 |
| 2003/0158597 A1 * | 8/2003 | Quiachon et al. | 623/1.23 |
| 2003/0225446 A1 * | 12/2003 | Hartley | 623/1.11 |
| 2005/0154439 A1 * | 7/2005 | Gunderson | 623/1.11 |
| 2006/0271151 A1 * | 11/2006 | McGarry et al. | 623/1.11 |
| 2007/0038178 A1 * | 2/2007 | Kusleika | 604/103.03 |

* cited by examiner

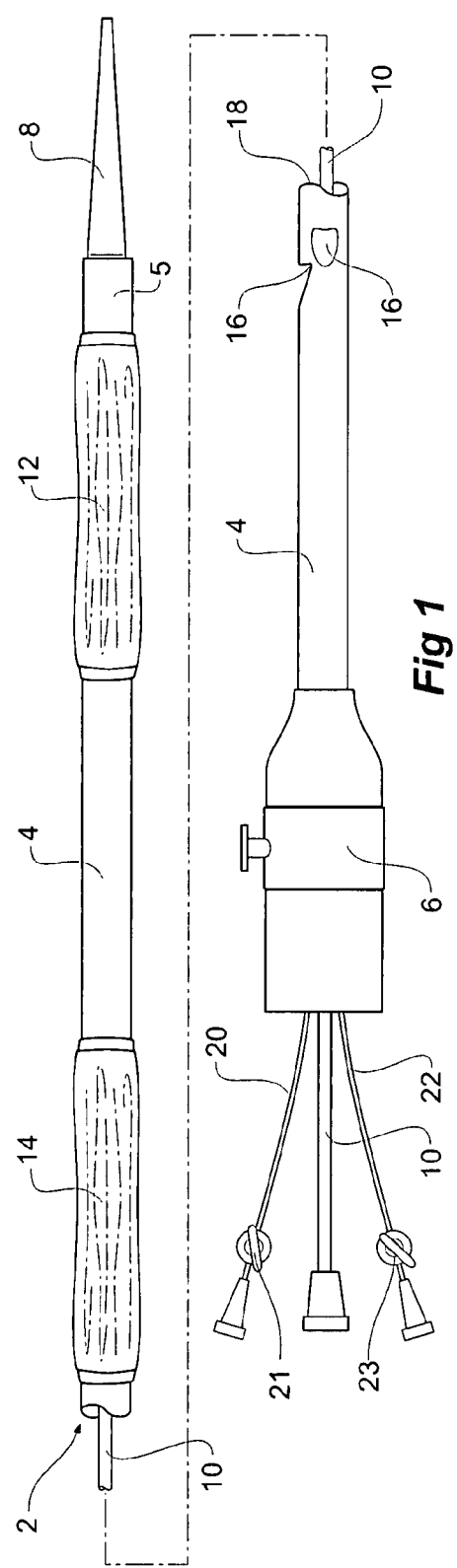
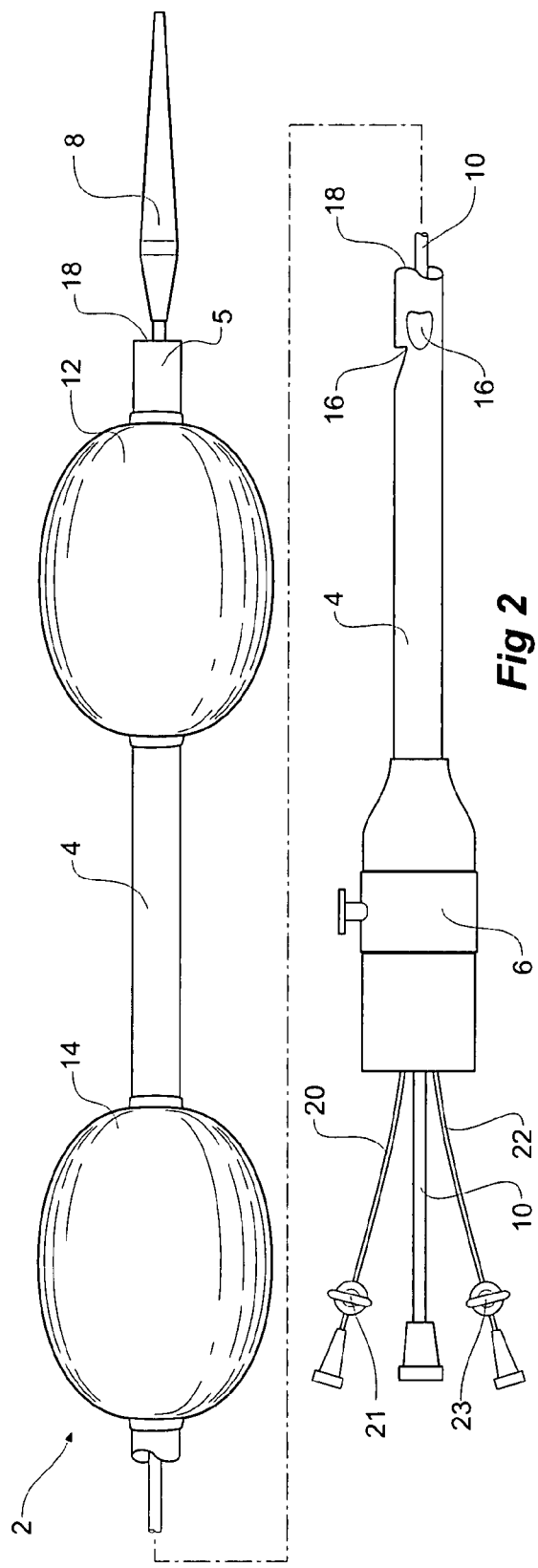
Fig 1
Fig 2

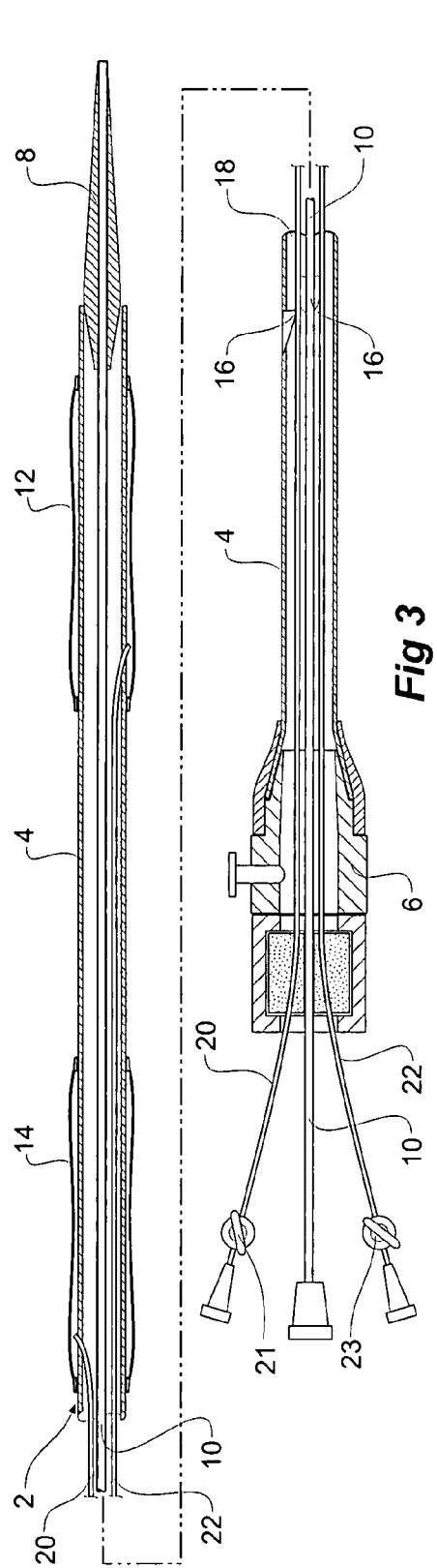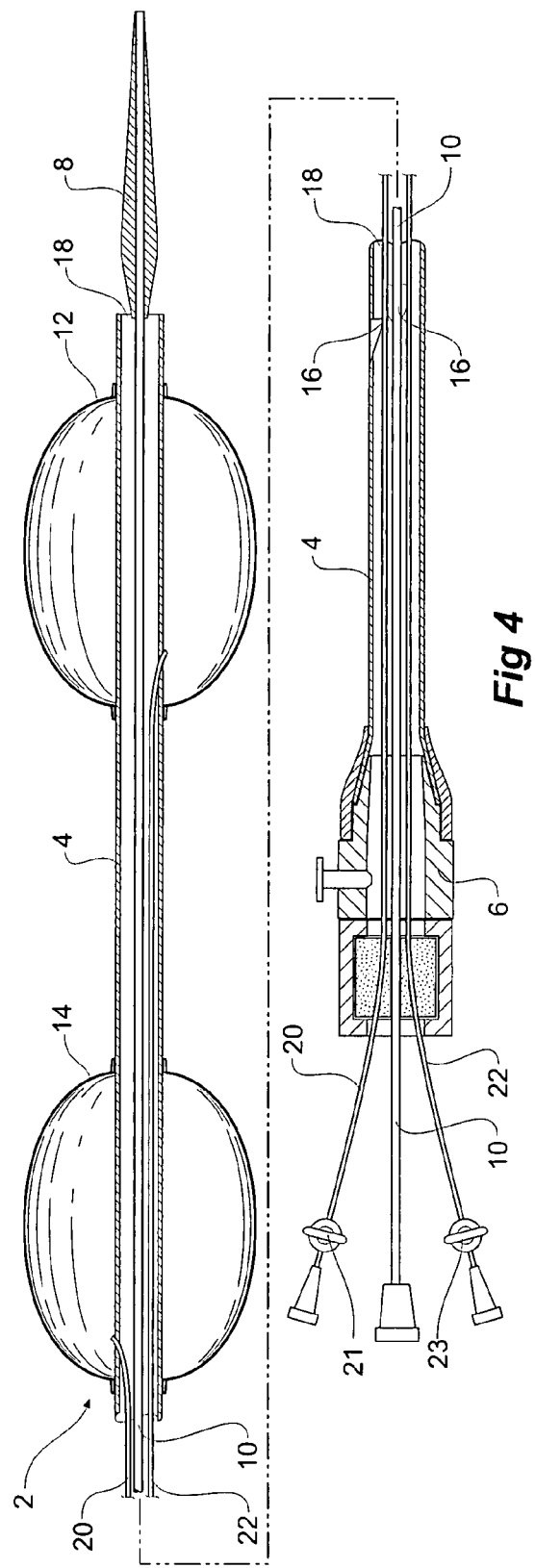

EMERGENCY TRANSECTION DEVICE

CROSS-REFERENCE TO RELATED APPLICATIONS

This application claims priority of provisional application Ser. No. 60/857,230, filed Nov. 7, 2006.

TECHNICAL FIELD

This invention relates to a medical device and more particularly to a device for assisting in the treatment in an emergency transection operation.

BACKGROUND OF THE INVENTION

In the case of a severe accident, such as a motor vehicle accident, the large blood vessels of the body, such as the aorta, may become damaged with accompanying severe hematoma in the region of the damage. Such damage may be termed a transection. In a transection the wall of the large vessels, such as the aorta, is damaged and is necessary for surgeon to perform an open chest surgery to repair the torn aorta. Because of the hematoma it may take some time for a surgeon to locate the area of the actual transection and make a suitable repair and in this time significant blood loss can occur.

It is the object of this invention to provide a blood bypass system to give the surgeon more time to make the necessary repair in the case of an emergency transection operation.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form therefore the invention is said to reside in an emergency transection intervention device comprising; an elongated catheter comprising a lumen therethrough, a nose cone dilator at a first end of the catheter and temporarily closing off the first end of the elongate catheter, a haemostatic seal on a second end of the catheter and closing off the second end of the elongate catheter, a guide wire catheter extending through the haemostatic seal and the elongate catheter to the nose cone dilator, first and second inflatable balloons spaced apart on the elongate catheter, and at least one aperture in the elongate catheter between the balloons and the haemostatic seal, whereby the emergency transection intervention device can be deployed into a blood vessel of the human or animal body with the balloons either side of a damaged portion of the vessel and the balloons inflated such that a region of the vessel between the balloons is isolated, the nose cone dilator advanced by moving the guide wire catheter through the haemostatic seal to allow blood flow into the lumen of the elongate catheter and through the elongated catheter to exit through the least one aperture in the elongate catheter.

Preferably inflation tubes for the first and second inflatable balloons extend through the lumen of the elongate catheter and the haemostatic seal or alternatively the inflation tubes exit the elongate catheter proximal of the haemostatic seal.

Preferably the inflation tubes each include a valve to close of the tube to hold inflation of the respective balloons.

The elongate catheter may be a thin walled flexible catheter and have a diameter of from 24 to 44 French. Hence the thin walled flexible catheter may have a diameter of from 3 to 6 mm and a wall thickness of from 0.1 mm to 0.3 mm.

In a preferred embodiment the balloons may be compliant balloons inflatable to a diameter of from 25 to 50 mm. The balloons can be spaced apart by from 50 to 150 mm.

It will be seen that by this invention there is provided a device which a surgeon can quickly deploy into the vessel such as the aorta using a Seldinger technique such that the balloons on the device are either side of the transection and with the balloons inflated blood pressure would be taken away from the region of the transection while still allowing blood flow through the elongate catheter entering at the nose cone dilator end when the nose cone dilator is extended and exiting the elongate catheter through the at least one aperture in the elongate catheter distal of the balloons.

After the transection has been repaired the balloons can be deflated, the device removed and the minor incision for the entry of the transection device can be repaired.

BRIEF DESCRIPTION OF THE DRAWING

This then generally describes the invention but to assists with understanding reference will now be made to the accompanying drawings which show preferred embodiments of the invention and one method by which the device of the present invention may be used.

In the drawings;

FIG. 1 shows a first embodiment of an emergency transection intervention device according to the present invention;

FIG. 2 shows the embodiment of FIG. 1 with the balloons inflated;

FIG. 3 shows a longitudinal cross-sectional view of the embodiment shown in FIG. 1;

FIG. 4 shows a longitudinal cross-sectional embodiment of the device shown in FIG. 2;

DETAILED DESCRIPTION

Figure 5:
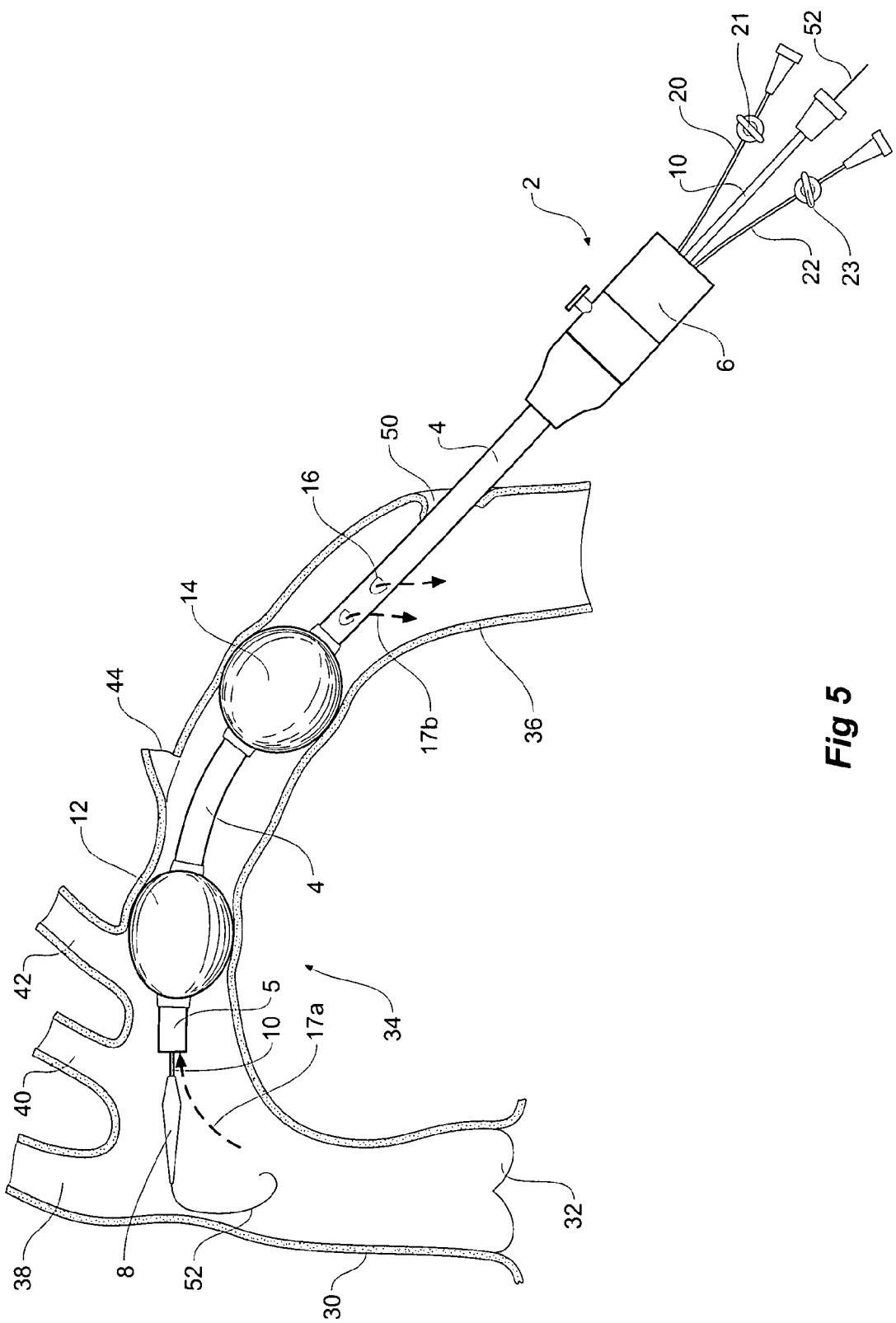
FIG. 5 shows a schematic view of part of the aorta of a patient with a device according to the present invention deployed into the aorta and with the balloons inflated.

Now looking at FIGS. 1 to 4 it will be seen that the emergency transection intervention device 2 comprises an elongate catheter 4 which extends from a handle and haemostatic seal 6 to a nose cone dilator 8. A guide wire catheter 10 extends through the haemostatic seal 6 and is fastened to the nose cone dilator 8. Along the elongate catheter 4 a proximal balloon 12 and a distal balloon 14. Distal of the distal balloon 14 there are apertures 16 in the elongate catheter 4 which allows access into the lumen 18 of the elongate catheter.

Balloon inflation tubes 20 and 22 extend through the haemostatic seal and handle 6 and extend through the elongate catheter to the respective balloons. The inflation tubes 20 and 22 have manually operable valves 21 and 23 respectively to close off the tubes to hold the inflation of the respective balloons.

Pressurized fluid such as saline can be directed through the tubes 20 and 22 to inflate the balloons 12 and 14 respectively as shown in FIGS. 2 and 4 and the valves 21 and 23 closed to hold the inflation of the balloons. The guide wire catheter 10 can then be advanced through the haemostatic seal to move the nose cone dilator proximally to open up the proximal end 5 of the elongate catheter. In its retracted position the nose cone dilator closes off the proximal end 5 of the elongate catheter.

FIG. 5 shows a schematic view of the vasculature of a patient in the region of the thoracic arch. The vasculature includes an ascending aorta 30 from an aortic valve 32 on the heart and then a thoracic arch 34 to a descending aorta 36. In the region of the thoracic arch 34 extend the brachiocephalic artery 38, the left carotid artery 40 and the left subclavian artery 42.

In this case because of a trauma such as a motor vehicle accident there has been a transection 44 high up in the descending aorta 36 and it is desirable to isolate that region of the aorta during repair of the transection.

The emergency transection intervention device 2 has been deployed into the descending aorta by the Seldinger technique at 50 over a pre-inserted guide wire 52. At that stage the nose cone dilator 8 is retracted so that it seals into the proximal end 5 of the elongate catheter 4. The emergency transection intervention device has been deployed such that the proximal balloon 12 is proximal of the transection 44 and the distal balloon 14 is distal of the transection 44. The device 2 is inserted into the vessel until the apertures 16 are within the vessel.

The balloons 12 and 14 are then inflated to the state they are shown in FIG. 5 so that they essentially isolate the descending aorta in the region of the transection 44 and the valves 21 and 23 closed to hold the inflation of the balloons. The guide wire catheter 10 is then advanced through the haemostatic seal and handle 6 until the nose cone dilator 8 is disengaged from the proximal end 5 of the elongate catheter 4. Blood can then flow as shown by the arrow 17a into and through the elongate catheter entering at the proximal end 5 and exiting at the apertures 16 as shown by the arrow 17b to allow continued blood flow to the descending aorta during the operation to repair the transection.

When the operation is completed the balloons 12 and 14 are deflated by opening the valves 21 and 23 and the nose cone dilator 8 is retracted back into the elongate catheter 4 and the entire device can then be withdrawn and the region 50 of the Seldinger puncture repaired.

The Seldinger technique is a medical procedure to obtain safe access to blood vessels and other hollow organs. It is named after Dr Sven-Ivar Seldinger (1921-1998), a Swedish radiologist, who introduced the procedure in 1953. The desired vessel or cavity is punctured with a sharp hollow needle called a trocar, with ultrasound guidance if necessary. A round-tipped guide wire is then advanced through the lumen of the trocar, and the trocar is withdrawn. The intervention device of the present invention can now be passed over the guide wire into the vessel. After passing a sheath or tube, the guide wire can be withdrawn.

In one embodiment the elongate catheter 4 may be a flexible thin walled tube having a diameter of from 24 to 44 French. The spacing between the proximal and distal balloons 12 and 14 may be from 50 mm to 150 mm. The balloons are preferably compliant balloons, that is they do not have a fixed expanded size and shape and hence can expand to the diameter and shape of the vessel in which they are inflated. This ensures that they can seal against a potentially irregular wall of a vessel. The preferred inflated diameter of the balloon without exceeding any elastic limit is from 25 mm to 50 mm.

The balloons can be formed from latex or silicone rubber.

The elongate catheter and handle and haemostatic seal may be Flexor Sheath and Captor Valve both sold by Cook Incorporated (Bloomington, Ind., USA).

Figure 6:
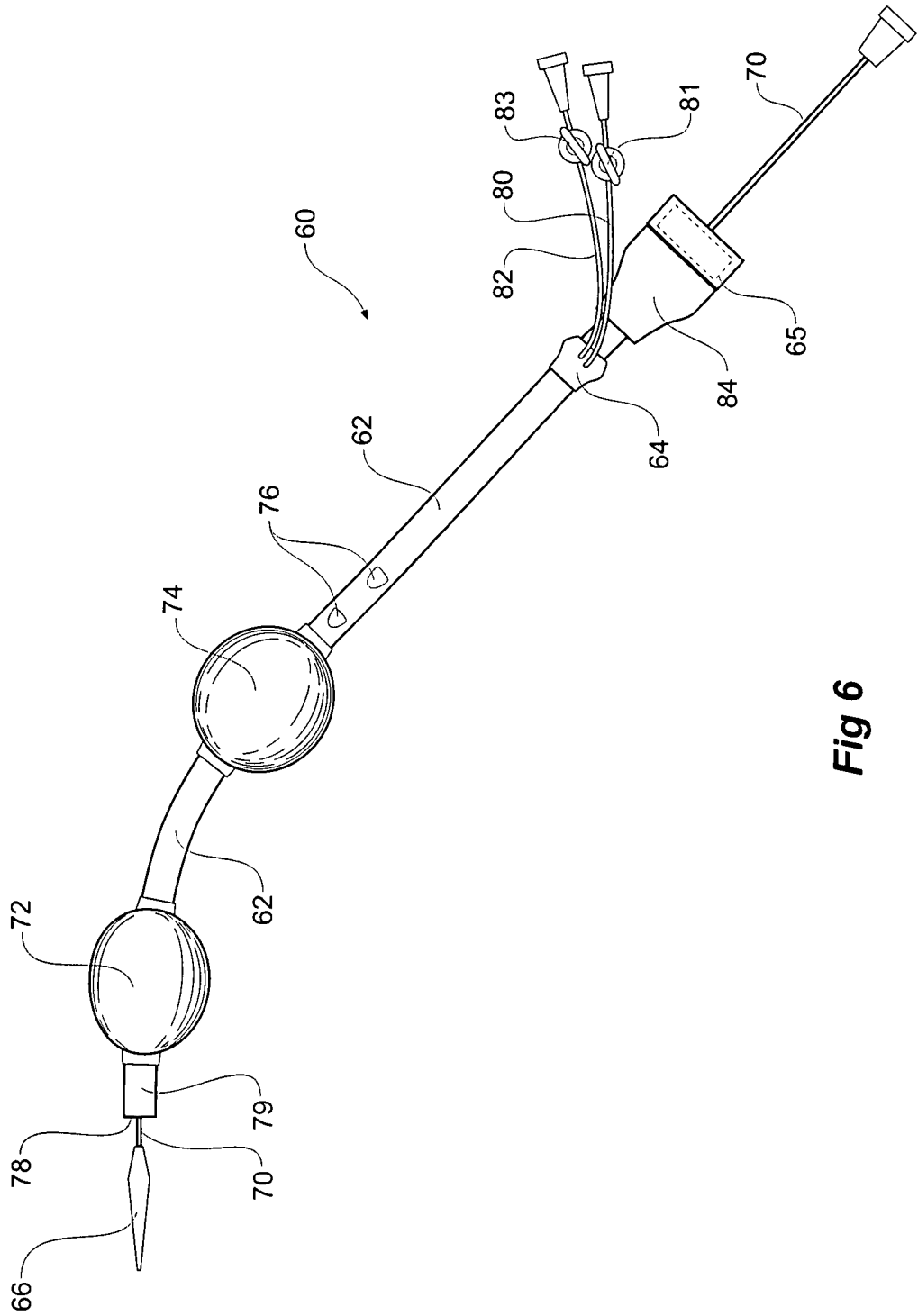
FIG. 6 shows an alternative embodiment of an emergency transection intervention device according to the present invention.

FIG. 6 shows an alternative embodiment of an emergency transection intervention device according to the present invention. In this embodiment it will be seen that the emergency transection intervention device 60 comprises an elongate catheter 62 which extends from a handle 64 and haemostatic seal 65 to a nose cone dilator 66. A guide wire catheter 70 extends through the haemostatic seal 65 and the elongate catheter 62 and is fastened to and extends through the nose cone dilator 66. Along the elongate catheter 62 there is a proximal balloon 72 and a distal balloon 74. Distal of the distal balloon 74 there are apertures 76 in the elongate catheter 62 which allow access into the lumen 78 of the elongate catheter.

Balloon inflation tubes 80 and 82 extend through a connector 84 on the elongate catheter 62 and extend through the elongate catheter to the respective balloons. The inflation tubes 80 and 82 have manually operable valves 81 and 83 respectively to close off the tubes to hold the inflation of the respective balloons.

Pressurized fluid such as saline can be directed through the tubes 80 and 82 to inflate the balloons 72 and 74 respectively. The guide wire catheter 70 can be advanced through the haemostatic seal 65 to move the nose cone dilator proximally to open up the proximal end 79 of the elongate catheter. In its retracted position the nose cone dilator closes off the proximal end 79 of the elongate catheter.

The device according to the present invention may be held as an emergency device in an emergency trauma operating theatre and used as necessary.

Throughout this specification various embodiments of the invention have been discussed but the invention is not limited to any one of them but may reside in two or more combined together in part or in whole. The examples are given for illustration only and not for limitation.

What is claimed is:

1. An aorta emergency transection intervention device comprising:
   an elongate catheter comprising a lumen extending entirely therethrough, the catheter comprising a first end and a second end, the lumen of the elongate catheter extending from the first end to the second end;
   a nose cone dilator at the first end of the elongate catheter, the nose cone dilator being movable with respect to the elongate catheter from a first position in which it temporarily closes off the first end of the elongate catheter to a second position in which it is disengaged from and is located proximal of the first end of the elongate catheter and allows flow into the elongate catheter;
   a haemostatic seal on the second end of the elongate catheter and closing off the second end of the elongate catheter;
   a guide wire catheter extending through the haemostatic seal and the elongate catheter, the guidewire catheter disposed within the lumen of the elongate catheter and affixed to the nose cone dilator, the nose cone dilator and the guidewire catheter comprising a lumen, the lumen extending through the nose cone dilator and the guidewire catheter, whereby the nose cone dilator can be moved from the first position to the second position by means of moving the guide wire catheter;
   a first proximal inflatable balloon and a second distal inflatable balloon spaced apart on the elongate catheter, wherein the elongate catheter between the first balloon and the second balloon has a solid, unperforated wall so as to prevent access through the wall;

at least one aperture in the elongate catheter between the second distal inflatable balloon and the haemostatic seal and in communication with the lumen of the elongate catheter; and whereby the emergency transection intervention device can be deployed into a blood vessel of a human or animal body with the balloons on either side of a damaged portion of the vessel and the balloons can be inflated such that a region of the vessel between the balloons is isolated and the nose cone dilator advanced from the first position to the second position by moving the guide wire catheter through the haemostatic seal to allow blood flow through the first end of the elongate catheter into the lumen of the elongate catheter and through the elongate catheter to exit through the at least one aperture in the elongate catheter.

2. An emergency transection intervention device as in claim 1 wherein inflation tubes for the first and second inflatable balloons extend through the lumen of the elongate catheter and the haemostatic seal.

3. An emergency transection intervention device as in claim 2 wherein the inflation tubes each include a valve to close off the tube to hold inflation of the balloons.

4. An emergency transection intervention device as in claim 1 wherein the elongate catheter is a thin walled flexible catheter and has a diameter of from 24 to 44 French.

5. An emergency transection intervention device as in claim 1 wherein the balloons are compliant balloons inflatable to a diameter of from 25 to 50 mm.

6. An aorta emergency transection intervention device comprising:

an elongate catheter comprising a lumen extending entirely therethrough, the catheter comprising a first end and a second end, the lumen of the elongate catheter extending from the first end to the second end;

a nose cone dilator at the first end of the elongate catheter, the nose cone dilator being movable with respect to the elongate catheter from a first position in which it temporarily closes off the first end of the elongate catheter to a second position in which it moves away from the first end of the elongate catheter and allows flow into the elongate catheter;

a haemostatic seal on the second end of the elongate catheter and closing off the second end of the elongate catheter;

a guide wire catheter extending through the haemostatic seal and the elongate catheter, the guidewire catheter disposed within the lumen of the elongate catheter and affixed to the nose cone dilator, the nose cone dilator and the guidewire catheter comprising a lumen, the lumen extending through the nose cone dilator and the guidewire catheter, whereby the nose cone dilator can be moved from the first position to the second position by means of moving the guide wire catheter;

a first proximal inflatable balloon and a second distal inflatable balloon spaced apart on the elongate catheter, wherein the elongate catheter between the first balloon and the second balloon has a solid, unperforated wall so as to prevent access through the wall;

at least one aperture in the elongate catheter between the second distal inflatable balloon and the haemostatic seal and in communication with the lumen of the elongate catheter; and whereby the emergency transection intervention device can be deployed into a blood vessel of a human or animal body with the balloons on either side of a damaged portion of the vessel and the balloons can be inflated such that a region of the vessel between the balloons is isolated and the nose cone dilator advanced from the first position to the second position by moving the guide wire catheter through the haemostatic seal to allow blood flow through the first end of the elongate catheter into the lumen of the elongate catheter and through the elongate catheter to exit through the at least one aperture in the elongate catheter.

7. An aorta emergency transection intervention device comprising:

an elongate catheter comprising a lumen extending entirely therethrough, the catheter comprising a first end and a second end, the lumen of the elongate catheter extending from the first end to the second end;

a nose cone dilator at the first end of the elongate catheter, the nose cone dilator being movable with respect to the elongate catheter from a first position in which it temporarily closes off the first end of the elongate catheter to a second position in which it moves away from the first end of the elongate catheter and allows flow into the elongate catheter;

a haemostatic seal on the second end of the elongate catheter and closing off the second end of the elongate catheter;

a guide wire catheter extending through the haemostatic seal and the elongate catheter, the guidewire catheter disposed within the lumen of the elongate catheter and affixed to the nose cone dilator, the nose cone dilator and the guidewire catheter comprising a lumen, the lumen extending through the nose cone dilator and the guidewire catheter, whereby the nose cone dilator can be moved from the first position to the second position by means of moving the guide wire catheter;

a first proximal inflatable balloon and a second distal inflatable balloon spaced apart on the elongate catheter;

at least one aperture in the elongate catheter between the second distal inflatable balloon and the haemostatic seal and in communication with the lumen of the elongate catheter;

whereby the emergency transection intervention device can be deployed into a blood vessel of a human or animal body with the balloons on either side of a damaged portion of the vessel and the balloons can be inflated such that a region of the vessel between the balloons is isolated and the nose cone dilator advanced from the first position to the second position by moving the guide wire catheter through the haemostatic seal to allow blood flow through the first end of the elongate catheter into the lumen of the elongate catheter and through the elongate catheter to exit through the at least one aperture in the elongate catheter; and wherein the elongate catheter between the first balloon and the second balloon has a solid, unperforated wall so as to prevent access through the wall.

8. An emergency transection intervention device as in claim 7 wherein in the second position the nose cone dilator is disengaged from and is located proximal of the first end of the elongate catheter and allows flow into the elongate catheter.

* * * * *